United States Patent [19]

Menard

[11] Patent Number: 4,507,163

[45] Date of Patent: Mar. 26, 1985

[54] IMPARTING AN INELASTIC AND ELASTIC CHARACTER TO PREDETERMINED PORTIONS OF AN ELASTIC WEB FOR USE IN MAKING DISPOSABLE DIAPERS

[75] Inventor: Michael J. Menard, Bourbonnais, Ill.

[73] Assignee: Johnson & Johnson Baby Products Company, New Brunswick, N.J.

[21] Appl. No.: 296,934

[22] Filed: Aug. 27, 1981

[51] Int. Cl.³ .............................................. B32B 31/08
[52] U.S. Cl. .................................. 156/164; 156/229; 156/269; 156/305; 264/342 RE
[58] Field of Search ................ 156/164, 229, 83, 495, 156/269, 305; 264/341, 342 R, 342 RE; 128/287

[56] References Cited

U.S. PATENT DOCUMENTS

| | | | |
|---|---|---|---|
| 3,443,009 | 5/1969 | Chirgwin | 264/342 RE |
| 3,445,561 | 5/1969 | Huff et al. | 264/342 RE |
| 3,493,646 | 2/1970 | Larkin et al. | 264/342 RE |
| 3,973,905 | 8/1976 | Wilson | 264/342 RE |
| 4,081,301 | 3/1978 | Buell | 156/164 |
| 4,239,578 | 12/1980 | Gore | 156/164 |
| 4,300,967 | 11/1981 | Sigl | 156/164 |
| 4,309,236 | 1/1982 | Teed | 156/164 |
| 4,337,771 | 7/1982 | Pieniak | 128/287 |

Primary Examiner—Jerome Massie
Attorney, Agent, or Firm—Martha A. Michaels; Nancy A. Bird

[57] ABSTRACT

This invention relates to an improved method for rendering discrete portions of a moving web with an elasticized character while preserving the inelastic character of the remaining portions of the substantially inelastic web. The method is especially suitable for use in the manufacture of disposable diaper components and the like.

9 Claims, 6 Drawing Figures

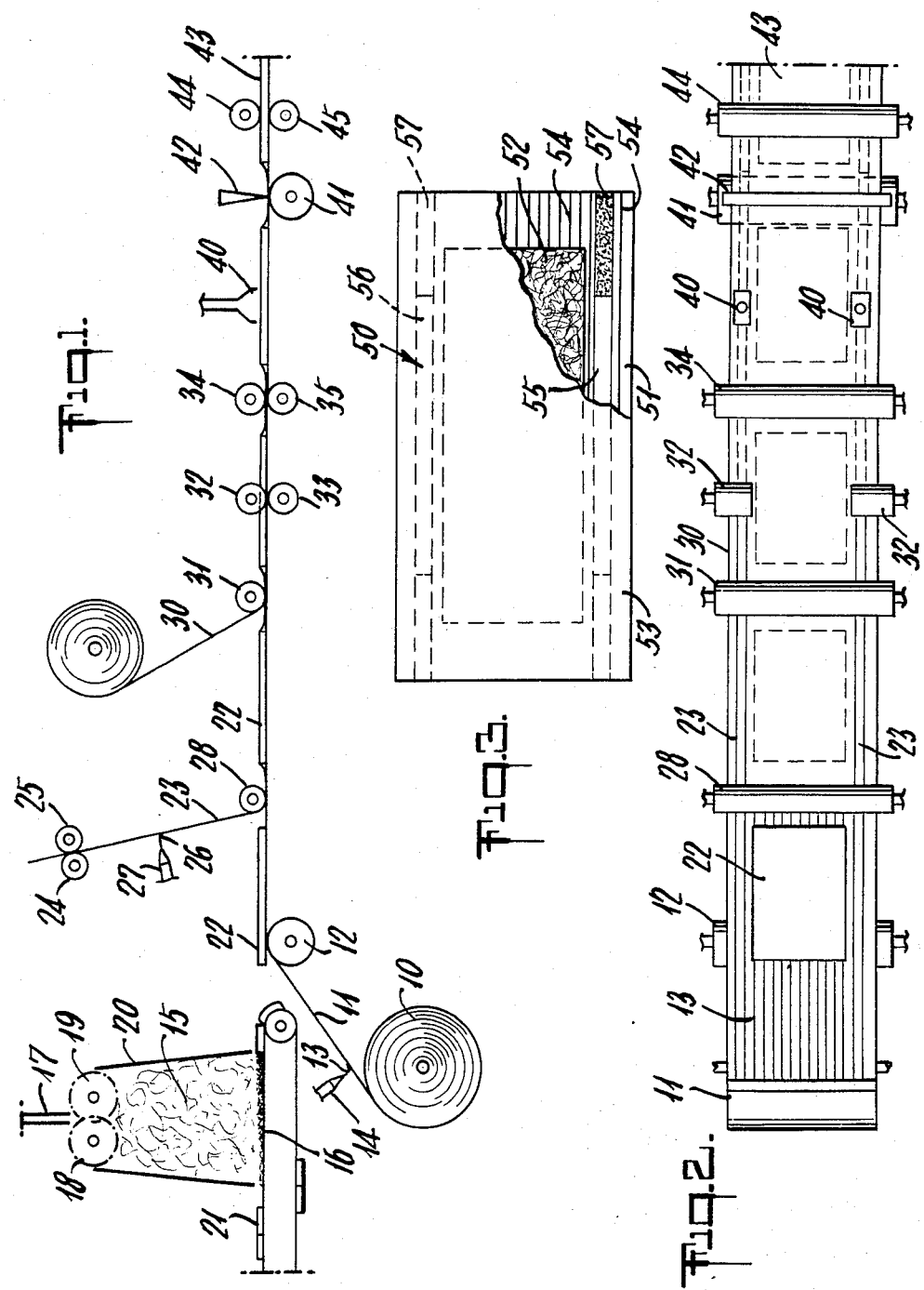

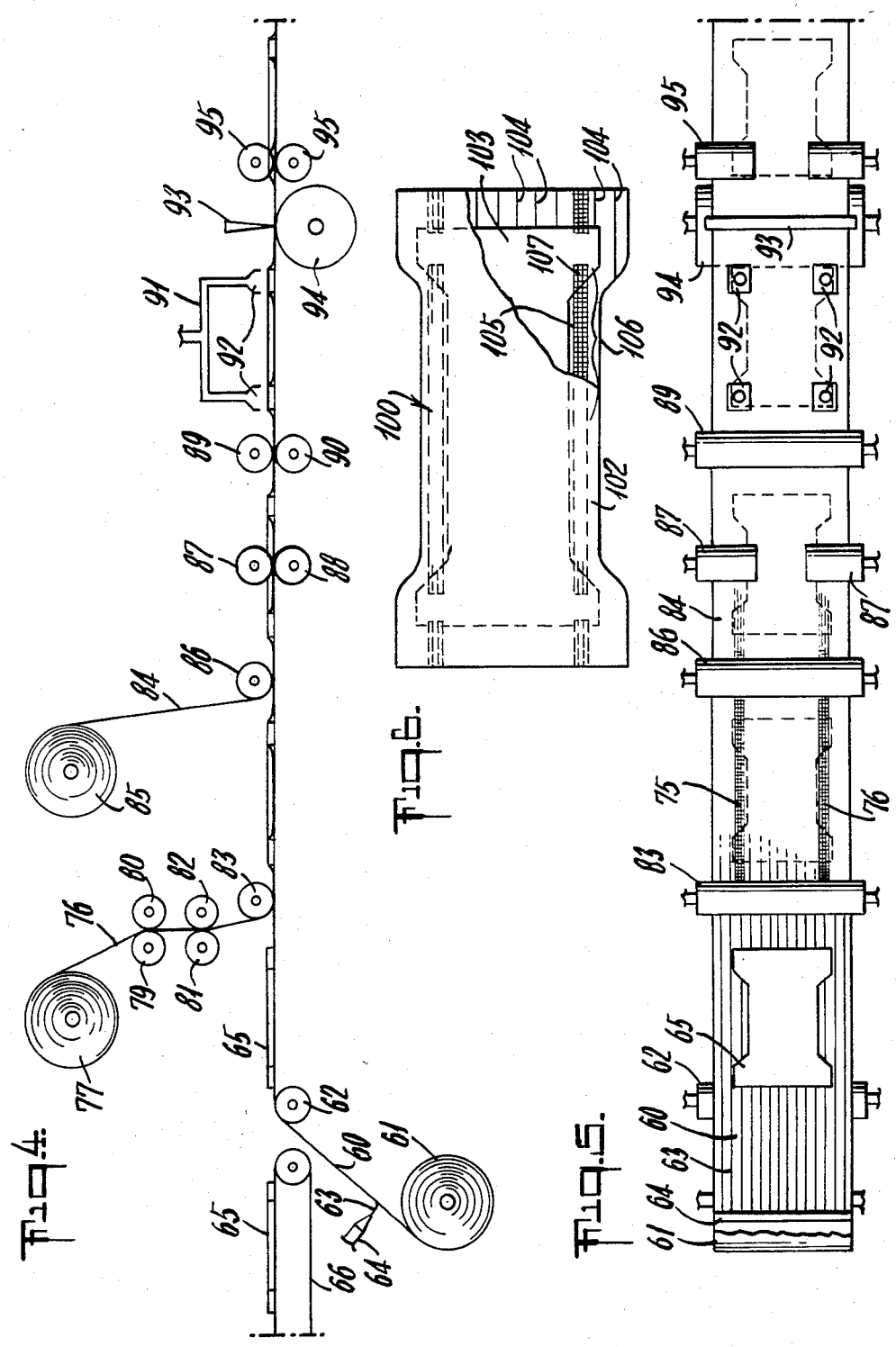

IMPARTING AN INELASTIC AND ELASTIC CHARACTER TO PREDETERMINED PORTIONS OF AN ELASTIC WEB FOR USE IN MAKING DISPOSABLE DIAPERS

BACKGROUND OF THE INVENTION

Methods are known for affixing an elastic member or element, such as an elastomeric band or ribbon to a flexible substantially inelastic web of material defining clothing or components thereof including briefs, panty briefs, disposable diapers and the like.

Methods are known for applying an elastic element to a continuously moving web. U.S. Pat. No. 3,838,367 to Bourgois discloses a method for securing a stretched elastic element to a nonelastic fabric web and maintaining the assembled element on the web in a stretched condition until cut transversely in the direction of travel to produce separate panels. U.S. Pat. No. 4,081,301 to Buell cites other prior art patents showing ways in which an elastic ribbon is joined to a moving web of material. The Buell patent itself discloses a method and apparatus for continuously attaching discrete lengths of elastic ribbon to a moving web. The elastic ribbon is fed in a stretched condition to the web and the elastic ribbon is intermittently secured to predetermined regions of the web while so stretched. Subsequently, the web and elastic ribbon are transversely cut in an area where the elastic ribbon is not secured to the web. This step forms severed unadhered portions of elastic at both ends of each discrete length of said elastic ribbon adhered to the web. The separate unadhered ends of the elastic ribbon are allowed to relax and contract to their unstretched state.

In U.S. Pat. No. 4,337,771, Pieniak et al, there is disclosed a diaper having an elastic member disposed along both longitudinal edges. The central portion of the members are allowed to remain elastic to gather the central portion while the areas adjacent these gathered areas have been rendered inelastic to reinforce the marginal portions of the diaper. The technique for rendering the marginal areas, inelastic is to provide excess energy to the marginal areas such as with heat or ultrasonics, to render the area inelastic. Also in copending commonly assigned patent application Ser. No. 253,419, filed Apr. 13, 1981, there is disclosed a technique for incorporating stretched elastics into inelastic webs wherein heat is used to sever the elastic and render desired areas inelastic. Heat is also used to adhere the desired inelastic areas to the web.

In many of these prior art methods, in order to obtain the desired inelastic and elastic areas, adhesives must be applied in such an intermittent manner. This requires that the adhesive be precisely controlled for exact deposition. It also requires intermittently operated securing mechanisms such as adhesive applicators. Such mechanisms are very hard to operate in high speed manufacturing operations to apply intermittent, exact length glue lines. In others of these methods where the adhesive is applied continuously and heat or some outer technique is then used to render areas inelastic, the heat or other technique must be applied and must function substantially instantaneously in order to be effective. Again, an extremely difficult step to accomplish in high speed manufacturing operations. Also, when manufacturing unitized disposable diapers which have a thermoplastic film backing the application of heat becomes even more complicated because of the possible deleterious effects the heat may have on the thermoplastic film backing.

SUMMARY OF THE INVENTION

According to the present invention we have discovered an improved method for securing an elastic member to a continuously moving, flexible, generally inelastic web of material such as material defining disposable diaper components and the like to impart a stretchable characteristic at predetermined portions of the components while preserving in other portions the generally inelastic characteristic of the components. Our improved method, if desired, allows for the continuous application of adhesive. Also, our improved method provides economic advantages in the manufacturing operation in that our improved technique for rendering areas inelastic actually is allowed to move with the rapidly moving web while it is performing its function of rendering areas inelastic.

In accordance with the present invention, a web of inelastic material is moved along a path. An elastic member in a stretched condition has adhesive applied to one surface thereof. The adhesive coated surface of the elastic member is then combined or placed on the moving inelastic web. If desired, the adhesive may be applied to the web first and the stretched elastic member applied on top of the adhesive. It is preferred that the adhesive be applied continuously along the entire length of the stretched elastic member. Once the stretched elastic member is disposed on the moving inelastic web, intermittent areas of the stretched elastic member are treated with a solvent for the stretched elastic member to render the treated areas inelastic.

In a preferred embodiment of the method of the present invention, a continuous impermeable backing member is fed to a securement zone. A pair of stretched elastic members having adhesive applied continuously on one of their surfaces are also fed to the securement zone. The elastic members are disposed along the longitudinal edges of the backing member and generally parallel to the longitudinal edges with the surface carrying the adhesive disposed adjacent the backing member. Spaced apart absorbent panels are also fed to the backing member and a continuous permeable facing member is fed to the top surface of the panels. The facing member is substantially coextensive with the backing member. The longitudinal side margins of the backing and facing are pressed together adjacent the edges of the panel to secure the backing to the facing. The ends of the elastic member, that is, the portion of the elastic members between panels and in certain embodiments at the ends of the panels, are rendered inelastic by treating those portions of elastic members with a solvent for the elastic member. The laminate is then severed between panels to form individual laminated products, i.e., disposable diapers. In certain embodiments of the present invention the solvent for the elastic member may be applied to the entire area of the elastic member that it is desired to be rendered inelastic, while in other embodiments the solvent may be applied just at the ends of the portions that it is desired to render inelastic and the solvent allowed to sever the elastic member. In those instances where the elastic member is severed, the severed portion is allowed to contract and, hence, be rendered inelastic.

At best, it is seen that the present invention yield desirable and beneficial results, results which are not only new and different, but which also provide a substantial improvement over the prior art.

Numerous other advantages of the present invention will become readily apparent from the following detailed description of the invention and the various embodiments thereof as follows from the claims and the accompanying drawings.

BRIEF DESCRIPTION OF THE DRAWINGS

FIG. 1 is a side elevational schematic view of one form of apparatus for carrying out the method of the present invention;

FIG. 2 is a top plan view of the apparatus depicted in FIG. 1;

FIG. 3 is an enlarged plan view of one type of diaper product made in accordance with the method of the present invention;

FIG. 4 is a side elevational schematic view of another form of apparatus for carrying out the method of the present invention;

FIG. 5 is a top plan view of the apparatus depicted in FIG. 4; and

FIG. 6 is a plan view of another disposable diaper product made in accordance with the method of the present invention.

DETAILED DESCRIPTION OF THE DRAWINGS

Referring to FIGS. 1 and 2 of the drawings, a supply roll 10 of a substantially inelastic web 11 is fed about guide roll 12 and by appropriate nozzles 14. A batt of wood pulp fibers may be formed by depositing fibers 15 on a foraminous conveyor belt 16. Wood pulp board 17 is fed to a pair of rotating toothed rolls 18 and 19 which grind the pulp board and individualize the fibers and deposit the individualized fibers from an air duct 20 on the foraminous belt. The foraminous belt has spaced apart areas 21 which have been blocked to prevent deposition of the wood pulp fibers in those areas and, hence, produce spaced apart batts 22 of absorbent wood pulp fibers. These spaced apart batts of absorbent wood pulp fibers are fed to the surface of the substantially inelastic web. A stretched elastic member 23 is fed from a pair of stretching rolls 24 and 25. Actually, the elastic member is stretched by two sets of rolls. The first set, not shown, operates at a slower peripheral linear speed than the second set 24 and 25 so that the elastic member is stretched between the two sets of rolls as is well known in the art. Adhesive 26 is applied from a suitable nozzle 27 to the surface of the elastic members and the elastic members guided about a rotatable roll 28 parallel to the longitudinal edges of the substantially inelastic web outside the longitudinal edges of the absorbent batt of wood pulp fibers. A second substantially inelastic web 30 is fed about a guide roll 31 to the top surface of the absorbent panels. Compressing rolls 32 and 33 along both longitudinal edges compress the area outside the longitudinal edges of the absorbent panel to adhere the elastic member to the inelastic web. Adhesive 13 is applied by appropriate nozzle 14 to the surface of the inelastic web in a pattern of parallel lines. This adhesive is used to secure the entire laminate as will become clear in the ensuing description. The laminate then passes between a pair of intermittently operating nip rolls 34 and 35 which compress and adhere together the area between the spaced apart absorbent panels. These compressing nip rolls are operated intermittently so that they do not compress the areas containing the absorbent batts but only the areas between absorbent batts. The stretched elastic members now secured in place pass under a solvent spray station 40. The solvent spray station is operated intermittently so that it only sprays solvent onto the area of the stretched elastic member at the ends of the absorbent batt and in the area between adjacent absorbent batts to render the treated areas inelastic by the action of the solvent. The laminate passes over an anvil roll 41 and is cut by a suitable knife 42 into individual disposable diapers 43 which are conveyed away by a pair of conveying rolls 44 and 45 for suitable folding and packaging.

FIG. 3 shows a disposable diaper made in accordance with the method described in conjunction with FIGS. 1 and 2. The diaper 50 comprises an inelastic backing web 51, an absorbent batt 52 spaced inwardly from the longitudinal and transverse edges of the backing web, and an inelastic facing web 53. The inelastic facing web is coextensive with the backing web and is adhered thereto by suitable adhesive 54 around the marginal edges of the absorbent batt. Along each longitudinal edge is a stretched elastic member 55 and 56. The elastic member acts to gather the laminate in the central portion of the diaper but at the ends 57 of each elastic member the elastic has been rendered inelastic by the treatment with solvent so as not to gather that portion of the laminate.

Referring to FIGS. 4 and 5 of the drawings a suitable backing material 60 is fed from a supply roll 61 to a conveying roller 62. Adhesive 63 is extruded through a plurality of nozzles 64 onto the backing material. A plurality of shaped absorbent panels 65 are fed from a conveyor 66 to the adhesive on the backing material. The absorbent panels are spaced apart an appropriate distance so as to produce individual disposable diapers. The absorbent panels have a general hourglass shape, that is, the center portion of the panel is narrower than the end portions of the panel. The center portion of the panel fits between the legs of the wearer while the end portions fit about the waist of the wearer.

A pair of elastic members 75 and 76 are fed from suitable supply rolls 77 to a first set of nip rolls 79 and 80 and then to a second set of nip rolls 81 and 82. The second set of nip rolls rotate at a peripheral speed greater than the first set of nip rolls in order to stretch the elastic member. The stretched elastic member passes about a guide roller 83 and each elastic member is positioned adjacent the longitudinal edge of the center portion of the absorbent panel. The elastic member contacts the adhesive on the backing adjacent the center portion of the panel and the elastic member is disposed on top of the panel at the end portions thereof. In a preferred embodiment of the present invention as shown in FIGS. 4 and 5, the elastic member is reticulated or has apertures in it so that the adhesive will bleed through the aperture of the elastic member and adhere the backing to the facing which is subsequently placed on the backing. After the elastic members are positioned on the backing, an appropriate facing material 84 is fed from a supply roll 85 about a guide roller 86 to the upper surface of the backing and panels. The portion of the laminate adjacent the center portion of the panel is compressed by the laminating rollers 87 and 88 to adhere the facing to the backing and to secure the elastic member therebetween. The laminating rollers are operated intermittently so that they only compress the laminate adjacent the center portion of the panel and they do not compress the wider end portions of the panel. The end portions of the panel, that is the portions where there is only facing and backing and not an absorbent panel, are then laminated to one another by laminating rollers 89 and 90. The laminating rolls 89 and 90 are operated intermittently so as not to compress the panel. The laminate then passes under a solvent spray station 91 having 4 heads 92 and solvent is intermittently sprayed onto the laminate. The solvent is sprayed so as to contact the stretched elastic member in the area over the wider end portions of the panel and to also contact the stretched elastic member in the area between absorbent panels. This renders those areas inelastic so that the only elastic area left is adjacent the narrow central portion of the absorbent panels. The laminate passes between a cutting knife 92 cooperating with an anvil roll 93 which sever the laminate at the mid-portion between absorbent panels to form a plurality of individual disposable diapers. The finishing diapers are carried forward by conveying rolls 94 for appropriate folding and packaging.

Referring to FIG. 6 there is depicted a plan view of a diaper 100 made in accordance with the method described in conjunction with FIGS. 4 and 5 with a portion of the diaper cut away for easy description. The diaper comprises an inpermeable backing member 101 and a permeable facing member 102. These two members are coextensive. Disposed therebetween is a substantially hourglass shaped absorbent panel 103. The panel is narrow in the center portion of the diaper and wider at the end portions. The panel is of such a size so as to form marginal edges around the entire perimeter of the diaper. A plurality of adhesive lines 104 applied to the impermeable backing member adhere the panel to the backing member and also allow for the adherence of the facing to the backing member about the peripheral edges of the panel. Disposed along each longtitudinal edge is a stretched reticulated elastic member 105. The elastic member is elastic adjacent the narrowed central portion of the panel 106 but has been rendered inelastic in the portions adjacent the central portion 107, that is the portion over the wider edge portions and to the ends of the diaper where the elastic has been rendered inelastic by treatment with a suitable solvent.

Panels which may be used when making diapers in accordance with the present invention are those made from various absorbent materials, for example, a multiplicity of crepe cellulose wadding layers or fluff cellulose fibers or wood pulp fibers. The preferred absorbent panels are those made with wood pulp fibers, usually airlaid material having a basis weight of approximately 0.3 to 0.35 grams per square inch. The basis weight will vary depending on the size and shape of the diaper and the use to which it is to be put; to wit, daytime, nighttime, toddler and the like. Suitable techniques for forming such panels are disclosed and described in U.S. Pat. Nos. 4,216,687 and 4,279,369.

The elastic members useful in accordance with the present invention may be made from materials having elongation of from 20 to 1,000% and preferably from about 50 to 500% with recoveries in the range of 20 to 100% and preferably from 70 to 100%. The material should have a force to stretch at 100% from about 30 to 2,000 grams. A specially suitable elastic member is that disclosed in copending commonly assigned patent application U.S. Ser. No. 134,369, filed Mar. 27, 1980, now abandoned. The elastic members may be made from various synthetic polymeric elastomeric materials. Preferably they are made from the thermoplastic elastomeric materials as are more fully disclosed and described in copending commonly assigned patent application U.S. Ser. No. 134,369, filed Mar. 27, 1980. The elastic members may be anywhere from $\frac{1}{4}$ to $1\frac{1}{2}$ inch in width or even wider and may be apertured or solid as desired. In a preferred embodiment, the material is an apertured or reticulated elastomeric material $\frac{3}{4}$ inch wide. The elastic members may be secured in the diapers by ultrasonic bonding, heat sealing, or by using any of the well known hot melt or liquid adhesive materials.

The solvents which may be used in the method of the present invention will depend, of course, on the composition of the elastic member being used. When thermoplastic elastic members are used any of the well-known solvents for such material such as methylenechloride, trichloroethylene, etc. may be used. The solvent used should be non-explosive, evaporate relatively rapidly, have no deleterious effects on any of the other components of the laminate, and not have any adverse environmental effects. Generally, these solvents will only attack the elastic member while it is under tension and will not attack the thermoplastic elastic members when they are in a relaxed state.

Our invention is especially useful when utilizing the reticulated material as described in conjunction with FIGS. 4 and 5. It is believed that when using a reticulated member there is more surface area available to be acted on by the solvent and, hence, the solvent is faster acting as compared to when a solid thermoplastic elastic member is used. Also, the reticulated member requires more tension be placed on the individual strands which also increases the action of the solvent. These are extremely important advantages when producing disposable diapers at high rates of speed because of the improved economics and the minimum of seconds and waste produced.

The facing materials which may be used in the products of the present invention may be nonwoven webs made of a mixture of fibers consisting predominantly of inexpensive short cellulosic fibers such as short wood pulp fibers or cotton linters in amounts of 75% to 98% the balance being textile length fibers such as rayon as described in U.S. Pat. No. 3,663,348 to Liloia et al. Other facing materials which are suitable for use in the disposable diapers of this invention can have fabric weights in the range of about 0.25 to 5 ounces per square yard and densities of less than 1.5 grams per cc. generally in the range of from 0.2 to 1 gram per cc. The dry strength of the facing sheet for a fabric having a weight of about $1\frac{1}{2}$ ounces per square yard is at least $1\frac{1}{2}$ pounds per inch of width in the machine direction and at least 0.1 pound per inch of width in the cross direction. Such fabrics have good elongation, good loft and drape characteristics. The facings may be apertured or unapertured as desired and the facings may be made of naturally occurring fibers, artificial fibers, synthetic fibers, or blends thereof. Typical facing sheets made of polyester type fibers may have a weight of 0.75 ounces per square yard. The facing may be the same size as, and coterminous with, the backing or, alternatively, the facing may be wider than the backing and have its side edges inwardly folded so that the facing is coterminous with the backing as is shown in FIG. 3 of U.S. Pat. No. 3,612,055. In the latter case the elastic members may be secured to the inwardly folded side edges of the facing. In addition facings may be made from nonapertured material such as nonwoven isotropic webs or apertured polyolefin or polyester films having a desired moisture permeability. In all of the aforementioned facings the material should be relatively hydrophobic so as to retard wicking within the facing.

Suitable backing material for products embodying the present invention are the opaque polyolefin films, for example, a polyethylene film about 0.001 inch thick. Another suitable material for this purpose is a polyethylene terephthalate film having a thickness of about 0.005 inch.

The foregoing description of the drawings is illustrative and is not to be taken as limiting, still other variations and modifications are possible without departing from the spirit and scope of the present invention.

What is claimed is:

1. In a method for attaching elastic members to discrete portions of a moving substantially inelastic web to impart an elasticized character to predetermined portions of the web while preserving the inelastic character of other portions of the web wherein said method secures substantially uniformly stretched elastic members to said moving web, the improvement comprising applying solvent for said elastic member in the portions where it is desired to preserve the inelastic character of the web.

2. A method for continuously attaching an elastic member to discrete portions of a moving substantially inelastic web to impart an elasticized character to predetermined portions of the web while preserving the inelastic character of other portions of the web said method comprising the steps of:
   (a) conveying a first substantially inelastic web;
   (b) feeding spaced apart absorbent panels to the inelastic web;
   (c) feeding a pair of stretched elastic members along the longitudinal edges of said absorbent panel;
   (d) feeding a second substantially inelastic web to the top surface of the absorbent panels;
   (e) laminating the second inelastic web to the first inelastic web at the marginal edges thereof to secure the elastic members between the web;
   (f) treating portions of said stretched elastic member at least in the area between absorbent panels with a solvent for said elastic member to render said areas inelastic; and
   (g) securing the laminate between adjacent absorbent panels to produce a plurality of individual laminated products.

3. A method according to claim 2 wherein the elastic members are reticulated members having openings and the second web is laminated to the first web through said openings.

4. A method according to claim 2 wherein the first and second webs are laminated together between adjacent absorbent panels before the laminate is severed between said panels.

5. A method of intermittently attaching elastic members intermediate opposed waistband portions of absorbent panels contained in a continuously moving web of interconnected disposable diapers to form a pair of discrete elastic leg bands in each of said diapers from said web, said method comprising:
   (a) continuously feeding a substantially inelastic substrate web;
   (b) applying adhesive to a surface of said web substrate said adhesive being disposed in a substantially uniform pattern over the surface of said substrate;
   (c) feeding spaced apart absorbent panel elements having wider opposing waistband portions and a narrowed central portion to the surface of said web carrying said adhesive, said web extending outside the panel elements along the entire longitudinal edges of said elements;
   (d) feeding a pair of stretched elastic members to said web substrate, said members being disposed adjacent the longitudinal edges of said panel elements in the narrowed central portion thereof and in contact with said adhesive on said web substrate and said members overlying the wider waistband portions of said panel elements;
   (e) feeding a second substantially inelastic web substrate to the upper surface of said panel elements, said second web being coterminous with said first web substrate and overlying said panel elements and said elastic members;
   (f) applying pressure to said first and second web substrates along the peripheral portion of the first and second webs to secure said elastic member and to laminate said first and second web substrates;
   (g) treating at least a portion of the stretched elastic member that overlie wider waistband portions of the panel elements with a solvent for said elastic member to render said treated portions inelastic; and
   (h) cutting said web substrates transversely between adjacent panel elements to produce a plurality of individual disposable diapers having a pair of discrete elastic leg bands.

6. A method according to claim 5 wherein the adhesive is applied to the web substrate in a plurality of parallel lines.

7. A method according to claim 5 wherein the elastic members are reticulated elastic members.

8. A method according to claim 5 or 7 wherein the entire portion of the elastic members that overlie the wider waistband portions of the panel elements is treated with a solvent.

9. A method according to claim 5, 7, or 8 wherein the portion of the stretched elastic member extending between panel elements is treated with a solvent for said member to render said portion inelastic.

* * * * *